United States Patent [19]
Byrne

[11] Patent Number: 4,476,723
[45] Date of Patent: Oct. 16, 1984

[54] DENSITY SENSOR
[75] Inventor: Paul Byrne, Plano, Tex.
[73] Assignee: Analog Data Systems, Dallas, Tex.
[21] Appl. No.: 475,045
[22] Filed: Mar. 14, 1983
[51] Int. Cl.³ .............................................. G01N 9/10
[52] U.S. Cl. ..................................... 73/453; 73/430
[58] Field of Search ................ 73/451, 452, 453, 454, 73/430

[56] References Cited
U.S. PATENT DOCUMENTS
4,134,301 1/1979 Erwin .................................... 73/453

Primary Examiner—James J. Gill
Assistant Examiner—John E. Chapman, Jr.
Attorney, Agent, or Firm—Jerry W. Mills; Gregory M. Howison; Nina Medlock

[57] ABSTRACT

A density sensor includes a stationary housing (12) and a reciprocating body (22) with a float (26) attached thereto to provide a buoyant force. The reciprocating body (22) is connected to a piston (32) by a reciprocating rod (34). The piston (32) is operable to move within a bore (30). A second piston (52) is also disposed in the bore (30) and is coupled to the piston (32) by a spring (54). A transducer (44) is disposed at the other end of the bore and is connected to the piston (52) through hydraulic fluid disposed in a hydraulic chamber (56). The spring (54) is functional to remove low frequency components of acceleration from the buoyant force and the hydraulic fluid disposed in the hydraulic chamber (56) is operable to remove high frequency acceleration components from the buoyant force. In this manner, the transducer (44) can be isolated from both high and low frequency acceleration components.

18 Claims, 2 Drawing Figures

U.S. Patent   Oct. 16, 1984   4,476,723
FIG. 1
FIG. 2
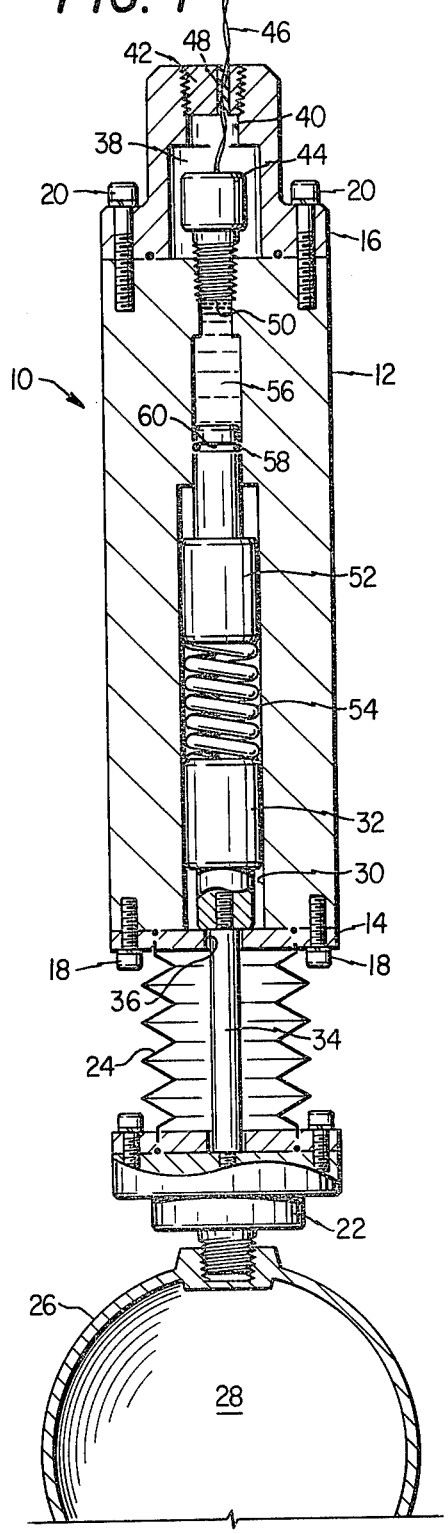
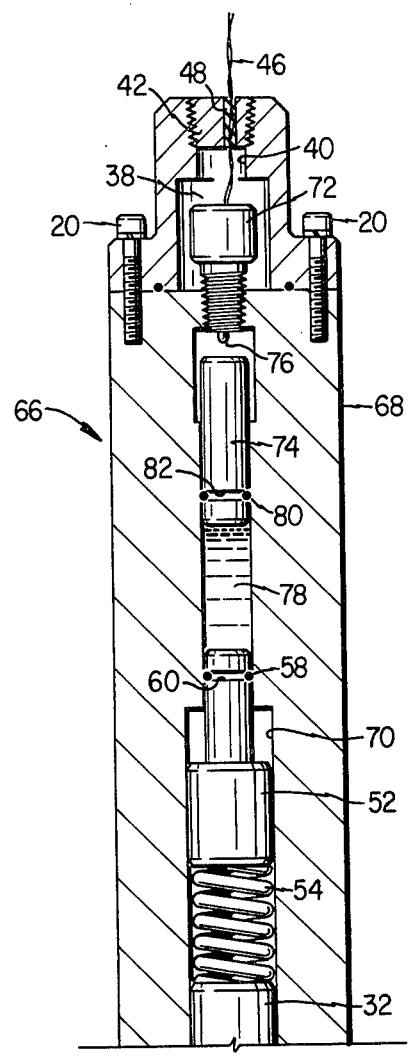

DENSITY SENSOR

TECHNICAL FIELD

The invention pertains in general to density sensors and, more particularly, to durable density sensors that are subjected to buoyancy forces with high and low frequency acceleration components.

BACKGROUND OF THE INVENTION

Density sensors are utilized to convert a buoyant force into an electrical signal through the use of a sealed float coupled to some type of transducer. To gain a high degree of accuracy, density sensors in the past have utilized a firm mechanical coupling to a transducer such as a load cell. This firm mechanical linkage allows the buoyancy force to be directly translated from the float to the load cell. Although this method of measuring the buoyant force is very accurate, it has the disadvantage of being very fragile. This is undesirable in applications in which these devices are submitted to environments with buoyant forces that have a high level of acceleration components associated therewith. These acceleration forces are the result of shock load forces that the float is subjected to in a working environment. These shock load forces subject the associated transducers to both very high and very low frequency acceleration force components that are particularly damaging to the transducers.

The transducers normally utilized in density sensors are the load cells which are basically a loaded beam attached to which are strain gauges. The strain gauge is an electro-mechanical device that converts strain into a resistive change. By incorporating this strain sensitive resistance into a balanced bridge circuit, an electrical signal can be generated that is proportional to the strain that the strain gauge is subjected to. To couple strain to the strain gauge from, for example, a loaded beam, it is necessary to utilize some form of adhesive. This adhesive is disposed between the loaded beam and the strain gauge and is subject to strain therein. This adhesive is the point at which strain gauges incur the most failures. Acceleration components contained in the shock load forces are readily transmitted through both the strain gauge and the loaded beam due to the high inertia thereof. However, the adhesive disposed therebetween has a much lower inertia resulting in very poor coupling of strain to the strain gauge. The result is that the adhesive fails and, consequently, the transducer must be replaced.

An example of a harsh environment in which density sensors are utilized is a mud pit in an oil field. These mud pits are typically subjected to very high turbulences which are required to maintain an equal density therein. Normally, a dedicated impeller is continually running to maintain this high turbulence. When density sensors are submerged in this type of environment, the high turbulences therein subject the density sensors to high shock load forces with components of very high frequency accelerations and also some low frequency acceleration components. These high frequency acceleration components are probably some of the most damaging forces that the density sensor can be subjected to, thereby resulting in very short mean time to failure rates for presently available density sensors. The low frequency acceleration components are primarily due to unusual forces, such as dropping the density sensor or allowing a hard object to impact the float on the density sensor. Since most density sensors utilize a fixed mechanical linkage between the float and the transducer, these high and low frequency acceleration forces are directly transmitted to the transducer thereby increasing the failure rates thereof.

In view of the above disadvantages, there is a need for a density sensor that is impervious to the components of high and low frequency accelerations that are present in the buoyant forces present in the harsh operating environments.

SUMMARY OF THE INVENTION

The present invention disclosed and claimed herein comprises a density sensor that utilizes a float for translating a buoyancy force to a sensor. The sensor converts the buoyancy force of the float into electrical signals. The buoyant force from the float is translated to the sensor through a hydraulic coupling such that high frequency acceleration components of the buoyant forces are attenuated therethrough.

In another embodiment of the present invention, a spring is inserted between the float and the hydraulic coupling to alternate acceleration components of the buoyant forces of a low frequency type. The combination of the spring and the hydraulic coupling allows translation of static buoyant forces while rejecting translation of both high frequency and low frequency acceleration components thereof that cause the greatest amount of damage to the density sensors.

BRIEF DESCRIPTION OF THE DRAWINGS

For a more complete understanding of the present invention and the advantages thereof, reference is now made to the following description taken in conjunction with the accompanying Drawings in which:

FIG. 1 illustrates a cross-sectional diagram of the density sensor of the present invention utilizing a pressure transducer; and FIG. 2 illustrates a cross-sectional diagram of an alternate embodiment of the density sensor utilizing a load cell.

DETAILED DESCRIPTION OF THE INVENTION

Referring now to FIG. 1, there is illustrated a cross-sectional diagram of a density sensor 10. The density sensor 10 has a stationary housing 12 with an end cap 14 disposed on one end thereof and an end cap 16 disposed on the other end thereof. The end cap 14 is attached to the stationary housing 12 with bolts 18 and the end cap 16 is attached to the housing 12 with bolts 20.

A reciprocating body 22 is attached to the end cap 14 through a bellows 24. In the preferred embodiment the bellows 24 is fabricated of stainless steel. A float 26 is attached to the reciprocating member 22 and has a sealed interior chamber 28 that is normally held at atmospheric pressure. The float 26 is operable to generate a buoyancy force when submerged in a liquid of a density other than that contained in the chamber 28. This buoyant force is translated to the reciprocating member 22. It should be understood that the float must be positioned such that the buoyant force is directed along the longitudinal axis of the housing 12.

The housing 12 has a bore 30 formed therein extending from the end cap 14 to the end cap 16 along the longitudinal axis thereof. A piston 32 is disposed in the bore 30 in sliding contact with the sides thereof. A reciprocating rod 34 has one end thereof attached to one end of the piston 32 and extends through an orifice 36 in the end cap 14. The reciprocating rod 34 passes through the bellows 24 and has the other end thereof attached to the reciprocating body 22 and is operable to translate the reciprocal motion of the reciprocating body 22 to the piston 32. The bellows 24 provides a seal between the exterior of the density sensor 10 and the interior of the bore 30 while allowing movement along the longitudinal axis of both the bore 30 and the reciprocating rod 34.

The end cap 16 has a sensor chamber 38 disposed therein which communicates with the exterior of the housing 12 through a conduit 40. A plug 42 seals the conduit 40 from the exterior environment of the density sensor 10. A pressure transducer 44 is disposed in the sensor chamber 38 and is threadedly inserted into the bore 30 of the housing 12. The electronic signals are carried on a pair of twisted wires 46 connected at one end thereof to the transducer 44 and then fed through a sealed orifice 48 in the plug 42 to a remote location. The transducer 44 has a pressure sensing surface 50 that is disposed within the bore 30 and is operable to translate an external pressure to the surface 50 to a shear force on a strain gauge internal to the transducer 44.

A piston 52 is disposed in the bore 30 in sliding contact therewith between the piston 32 and the sensing surface 50. A coil spring 54 is disposed between the piston 52 and the piston 32 with its compression axis aligned parallel to longitudinal axis of the housing 12. A hydraulic chamber 56 is defined between the surface 50 and the end of the piston 52 diametrically opposite the spring 54. An O-ring 58 is disposed in a groove 60 around the end of the piston 52 adjacent the hydraulic chamber 56. The O-ring 58 provides a fluid seal between the wall of the bore 30 and the outer surface of the piston 52. The diameter of the bore 30 around the hydraulic chamber 56 is smaller than the remaining portion of the bore 30. The hydraulic chamber 56 is dimensioned to provide the requisite amount of surface area for a predetermined amount of force per square unit area depending upon the particular type of pressure transducer utilized for transducer 44. The pressure transducer 44 in the preferred embodiment is available from ANALOG DATA SYSTEMS INC. The particular model employed depends upon the particular range of pressures that the pressure transducer will encounter.

In operation, the sensor 10 is submersed in a material having a density that is greater than the density of the air or fluid disposed in the float 26. The sensor 10 is oriented such that the buoyant force resulting from the differing density is oriented along the longitudinal axis of the bore 30 in the stationary housing 12 and directed towards the sensing surface 50 of the transducer 44. The resulting buoyant force urges the reciprocating rod 34 through the orifice 36 thereby compressing the bellows 24. In this manner, the buoyant force is translated to the piston 32. The piston 32 translates the buoyant force thereon through the spring 54 to the piston 52. The piston 52 then translates the buoyant force to the hydraulic fluid in the hydraulic chamber 56 and from there to the sensing surface 50. Under static conditions, the spring 54 undergoes a certain degree of compression depending upon the spring constant thereof. This effectively results in a direct translation of a static force therethrough. In a similar manner, the hydraulic fluid, which is a relatively incompressible fluid, directly translates the force from the piston 52 to the sensing surface 50. In pressure transducers utilizing internal strain gauges, there is normally a slight movement of the pressure sensing surface 50 thereby allowing the piston 52 to undergo a small displacement. Therefore, under static conditions, the force is directly coupled to the transducer 44 with virtually no attenuation.

When the float 26 is subjected to high shock load forces, the resulting forces delivered to the reciprocating body 22 are rich in high frequency acceleration components. The spring 54 effectively translates the high frequency acceleration components from the piston 32 to the piston 52 with relatively little attenuation thereof. However, an important aspect of the present invention is that the high frequency acceleration components are attenuated in passing through the hydraulic fluid in the hydraulic chamber 56. The hydraulic fluid in effect dampens the high frequency acceleration components and prevents them from reaching the pressure sensing surface 50 of the transducer 44 which can result in damage thereto.

When the float 26 is subjected to forces that are rich in low frequency acceleration components, such as a large soft impact, these acceleration components of the force are absorbed or attenuated by the spring 54. This is due to the compressibility of the spring which prevents translation of the low frequency acceleration components from the piston 32 to the piston 52. The hydraulic fluid in the hydraulic chamber 56, however, transmits the portion of these acceleration components that are translated to the piston 52.

Referring now to FIG. 2, there is illustrated a cross-sectional diagram of another embodiment of the present invention wherein like numerals refer to like parts in two figures. FIG. 2 illustrates a density sensor 66 which has a stationary housing 68 with a bore 70 formed therein. A force transducer 72 is disposed in the end of the bore 70 opposite the end that the piston 32 is disposed in. The transducer 72 is threadedly engaged into the end of the bore 70 to provide a seal therewith. The transducer 72 in the preferred embodiment is a load cell which accurately senses pressure through a rigid contact therewith.

A piston 74 is disposed in the bore 70 in sliding contact therewith and between the piston 52 and the transducer 72. One end of the piston 74 is disposed adjacent a pressure sensing member 76 of the transducer 72 and in contact therewith. The other end of the piston 74 and the end of the piston 52 diametrically opposite the spring 54 define a hydraulic chamber 78 that is filled with hydraulic fluid. An O-ring 80 is disposed in a groove 82 on the end of the piston 74 nearestmost the hydraulic chamber 78 to provide a seal with the sides of the bore 70.

The hydraulic fluid in the hydraulic chamber 78 provides a coupling between the bore 70 and the piston 74 that, as described above with reference to FIG. 1, absorbs any high frequency acceleration components of high shock load forces that may be translated from the float 26 to the piston 52. The piston 74 is operable to translate any static forces transmitted to and translated through the hydraulic fluid in the hydraulic sensor 78 directly to the sensing member 76 of the transducer 72. In this manner, any force components that are translated through the hydraulic fluid in the chamber 78 can be transmitted to the transducer 72 which is a load cell requiring a mechanical interface or coupling to the force. As described above with reference to FIG. 1, the diameter of the bore 70 at the hydraulic chamber 78 can be varied to determine the surface area of the pistons 52 and 74 which determines the force transmitted through the hydraulic fluid. Although not shown, the hydraulic chamber 78 can be segmented such that the piston 52 has a first cross-sectional area and the piston 74 has a second cross-sectional area at the surfaces adjacent the hydraulic chamber 78 to provide a ratio therebetween for distribution of the forces at the surfaces thereof.

In summary, a density sensor has been provided that translates a buoyant force from a float along a linear axis to a force transducer for sensing the force thereof and converting it to electronic signals. The buoyant force is coupled to the transducer through a spring that effectively attenuates any low frequency acceleration components of the force. In addition, the buoyant force is also coupled through a hydraulic fluid in a hydraulic chamber disposed in series with the spring that effectively attenuates any high frequency acceleration components that may be present in the buoyant force. In this manner, both high and low frequency acceleration components of the buoyant force can be attenuated to prevent damage to sensitive transducers such as strain gauges.

Although the preferred embodiment has been described in detail, it should be understood that various changes, substitutions and alterations can be made therein without departing from the spirit and scope of the invention as defined by the appended claims.

What is claimed is:

1. A density sensor, comprising:
   a float;
   means for sensing the buoyant force of said float;
   means for translating the buoyant force of said float to said means for sensing; and
   means for attenuating high frequency acceleration components present in the buoyant force of said float to prevent them from being translated by said means for translating to said sensor means.

2. The apparatus of claim 1 wherein said high frequency attenuation means is disposed between said translating means and said sensor means.

3. The apparatus of claim 1 wherein said high frequency attenuation means comprises hydraulic fluid disposed in a chamber connected to said sensing means at one end and to said translating means at the other end, the buoyant force transmitted through said chamber.

4. The apparatus of claim 3 wherein said transducer means comprises a pressure transducer.

5. The apparatus of claim 3 wherein said sensor means comprises a load cell.

6. The apparatus of claim 5 wherein said translating means comprises a first translating rod attached at one end to said float and a second translating rod attached at one end to said load cell, said first and second rods disposed in the bore of a cylinder and having the other end thereof in sealed sliding contact with the walls of the bore, said hydraulic fluid disposed between the other ends of said first and second translating rods in the bore of said cylinder to define said chamber.

7. The apparatus of claim 1 further comprising means for attenuating low frequency acceleration components present in the buoyant force from being translated by said means for translating to said transducer means.

8. The apparatus of claim 7 wherein said low frequency attenuation means comprises a spring.

9. A submersible density sensor, comprising:
   a float having a sealed inner chamber for exerting a buoyant force when submersed in a fluid having a different density than the inner chamber of said float;
   a cylinder having a bore formed therein;
   a translating rod disposed in said cylinder for sealed sliding contact with the walls of said bore and having one end thereof attached to said float for translating the buoyant force of said float along the longitudinal axis thereof;
   sensor means for sensing the buoyant force; and
   coupling means for coupling the translated force from said translating rod to said sensor means, said coupling means attenuating high frequency acceleration components present in the buoyant force translated from said float.

10. The apparatus of claim 9 wherein said sensor means comprises a pressure transducer for converting pressure to an electrical signal.

11. The apparatus of claim 10 wherein said pressure transducer is disposed at one end of said cylinder in sealing contact with said bore and said coupling means comprises hydraulic fluid disposed between the other end of said translating rod and said pressure transducer, said pressure transducer and the other end of said translating rod comprising a sealed chamber to contain said hydraulic fluid.

12. The apparatus of claim 9 wherein said sensor means comprises a load cell.

13. The apparatus of claim 12 wherein said load cell is disposed in the end of said cylinder opposite said float and said coupling means comprises a coupling rod disposed in said cylinder and in sealed sliding contact with the sides of the bore of said cylinder, one end of said coupling rod disposed adjacent said load cell, the other end of said coupling rod and the other end of said translating rod defining a sealed chamber within said cylinder, said chamber filled with hydraulic fluid for translating the buoyant force from said translating rod to said coupling rod, said hydraulic fluid reducing high frequency acceleration components present in the buoyant force from being translated to said load cell.

14. The apparatus of claim 9 wherein said coupling means further attenuates low frequency acceleration components present in the buoyant force such that said sensor means is not subjected to low frequency acceleration components of the buoyant force.

15. The apparatus of claim 14 wherein said coupling means comprises:
   a spring disposed in said cylinder and having one end thereof adjacent the other end of said translating rod, said spring attenuating low frequency acceleration components of the buoyant force;
   a coupling rod disposed in said cylinder and in sealed sliding contact with the interior walls of said bore, one end of said coupling rod disposed adjacent the other end of said spring;
   said sensor means comprising a pressure transducer disposed at the end of said cylinder opposite said translating rod and in sealing contact with the bore of said cylinder, said pressure transducer and the other end of said coupling rod forming a sealed chamber in the bore of said cylinder; and
   said chamber having hydraulic fluid disposed therein for translating forces from said coupling rod to said pressure transducer and reducing high frequency acceleration components of the force therethrough.

16. A submersible density sensor, comprising:

a float having a sealed inner chamber for exerting a buoyant force when submersed in a fluid having a different density than the inner chamber;

a cylinder having a bore formed therein and extending from one side of said cylinder to the other;

a translating rod disposed in the bore of said cylinder and having one end protruding therethrough, the other end thereof in sealed sliding contact with the sides of the bore in said cylinder, the other end of said translating rod attached to said float for translating the buoyant force of said float along the longitudinal axis thereof;

a spring disposed in the bore of said cylinder and having one end thereof adjacent the other end of said translating rod and compressible along the longitudinal axis of said cylinder to attenuate low frequency acceleration components present in the buoyant force;

a coupling rod disposed in the bore of said cylinder and in sealed sliding contact with the sides thereof, one end of said coupling rod disposed adjacent the other end of said spring;

a pressure transducer disposed in the end of said cylinder and in communication with the bore thereof, said pressure transducer in sealing contact therewith, said pressure transducer and the other end of said coupling rod forming a sealed chamber in the bore of said cylinder; and said chamber filled with hydraulic fluid for coupling forces from said coupling rod to said pressure transducer and attenuating high frequency acceleration components present in the buoyant force to prevent them from being translated therethrough.

17. A method for sensing density of a fluid, comprising:

translating buoyant force from a submerged float along a longitudinal axis;

sensing the buoyant force translated from the float and transforming the buoyant force into a corresponding electrical signal; and attenuating the translation of high frequency acceleration components present in the buoyant force prior to sensing the buoyant force.

18. The method of claim 17 further comprising attenuating low frequency acceleration components present in the buoyant force prior to sensing the buoyant force.

* * * * *